United States Patent
Luu et al.

(10) Patent No.: US 6,228,893 B1
(45) Date of Patent: May 8, 2001

(54) CYCLOHEXENONE LONG-CHAIN ALCOHOL AND MEDICAMENT CONTAINING SAME

(75) Inventors: Bang Luu; Gaby Schmitt; Florence Keyling; Celine Junges-Girlanda, all of Strasbourg (FR); Masashi Yamada; Yukie Suma, both of Tokyo (JP)

(73) Assignee: Meiji Milk Products Co., Ltd., Tokyo (JP)

( * ) Notice: Subject to any disclaimer, the term of this patent is extended or adjusted under 35 U.S.C. 154(b) by 0 days.

(21) Appl. No.: 09/463,972

(22) PCT Filed: Aug. 11, 1998

(86) PCT No.: PCT/JP98/03560

§ 371 Date: Feb. 14, 2000

§ 102(e) Date: Feb. 14, 2000

(87) PCT Pub. No.: WO99/08987

PCT Pub. Date: Feb. 25, 1999

(30) Foreign Application Priority Data

Aug. 13, 1997 (JP) .................................................. 9-218474

(51) Int. Cl.[7] .......................... A61K 31/12; C07C 49/713
(52) U.S. Cl. ......................... 514/690; 568/377; 568/378
(58) Field of Search .................................. 568/376, 377, 568/378; 514/690; 560/377

(56) References Cited

PUBLICATIONS

CA:129:144553 abs of Tetrahedron 54(27) pp. 7735–7748 by Girlanda–Junges et al., 1998.*
CA:125:185870 abs of WO9621438, Jul. 1996.*
CA:88:191159 abs of J Agric Food Chem 26(3) pp. 712–715 by Cyronak et al, 1978.*

* cited by examiner

Primary Examiner—Jean F. Vollano
(74) Attorney, Agent, or Firm—Oblon, Spivak, McClelland, Maier & Neustadt, P.C.

(57) ABSTRACT

Described is a cyclohexenone long-chain alcohol represented by the formula (1):

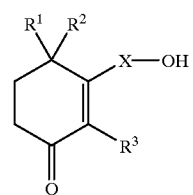

(1)

wherein R1, R2 and R3 each independently represents a hydrogen atom or a methyl group and X represents a C10–18 alkylene or alkenylene group. The cyclohexanone long-chain alcohol according to the present invention has excellent neurite growth stimulating effects and is therefore useful as a preventive and/or therapeutic agent for Alzheimer's disease.

17 Claims, No Drawings

CYCLOHEXENONE LONG-CHAIN ALCOHOL AND MEDICAMENT CONTAINING SAME

This application is the national stage of PCT/JP98/03560, filed Sep. 11/1998, now WO99/08987.

TECHNICAL FIELD

The present invention relates to a cyclohexenone long-chain alcohol having excellent neurite growth stimulating effects which is useful as preventive and/or therapeutic for cerebral diseases typified by dementia, and also as a medicament containing the same.

BACKGROUND ART OF THE INVENTION

Nerve growth factors (which will hereinafter be abbreviated as "NGF"s), many of which exist primarily in the hippocampus and cerebral cortex, are neurotrophic factors which stimulate differentiation or growth of neurocytes and are therefore essential for maintenance of function and survival. They act on catecholamine activating neurons in the peripheral nervous system, as well as on cholinergic neurons in the brain. Alzheimer's disease is thought to have, as its main lesion, degeneration and defluxion of cholinergic neurons. Therefore there has been an attempt to administer NGFs into the brain for the treatment of Alzheimer's disease. NGFs, however, cannot pass through the blood-brain barrier because they are proteins having molecular weights as high as 12,000. Therefore such treatment has not proven practical as a therepeutic method for humans. If there existed a low-molecular-weight compound which exhibited NGF-like effects and could pass through the blood-brain barrier or a compound capable of enhancing NGF synthesis in the brain, such a compound would likely be therapeutically useful for treating Alzheimer's disease. Based on this idea, substances exhibiting NGF-like effects have been sought. As a result, it has been shown that long-chain alcohols such as n-hexacosanol induce in vitro production of NGFs in gliacytes, thereby promoting neurite growth. In addition they can pass through the blood-brain barrier in vivo (Japanese Patent Application Laid-Open No. HEI 4-502167).

Effects of n-hexacosanol, however, have not been satisfactory yet.

An object of the present invention is therefore to provide a medicament comprising a compound which can be orally administered, which readily transfers into the brain, and which permits neurite growth in the brain even at low concentrations compared with those of the above-described long-chain alcohols such as n-hexacosanol.

DISCLOSURE OF THE PRESENT INVENTION

Focusing on the skeletal structure of cyclohexenone, the present inventors synthesized a number of cyclohexane derivatives. As a result, it has been found that a cyclohexenone long-chain alcohol represented by the below-described formula (1) is useful as a medicament for the prevention and treatment of cerebral diseases such as dementia because it has excellent neurite growth promoting effects even at lower concentrations compared with those of n-hexacosanol and has the effect of acting directly on the neurite, thereby stimulating neurite growth without inducing NGF production in gliacytes, leading to the completion of the present invention.

In one aspect of the present invention, there is thus provided a cyclohexenone long-chain alcohol represented by the following formula (1):

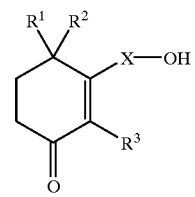

wherein $R^1$, $R^2$ and $R^3$ each independently represents a hydrogen atom or a methyl group and X represents a $C_{10-18}$ alkylene or alkenylene group.

In another aspect of the present invention, there is also provided a medicament comprising as an effective ingredient the compound represented by the formula (1).

In a further aspect of the present invention, there is also provided a neurite growth stimulating agent comprising the compound represented by the formula (1) as an effective ingredient.

In a further aspect of the present invention, there is provided a pharmaceutical composition comprising the compound represented by the formula (1) and a pharmaceutically acceptable carrier.

In a further aspect of the present invention, there is provided use of the compound represented by the formula (1) as a medicament.

In a further aspect of the present invention, there is provided a method for the treatment of dementia comprising administering to a patient an effective amount of the compound represented by the formula (1).

BEST MODES FOR CARRYING OUT THE INVENTION

In the formula (1), among the $C_{10-18}$ alkylene and alkenylene groups represented by X, preferred are $C_{10-18}$ alkylene groups, with $C_{10-16}$ alkylene groups being more preferred. For the alkylene or alkenylene group, either linear or branched one can be employed, with the linear one being more preferred. $R^1$, $R^2$ and $R^3$ each independently represents a hydrogen atom or a methyl group, with the case where at least one of them represents a methyl group being more preferred.

The compound of the present invention may exist in the form of a hydrate. The compound of the present invention has various isomers and these isomers are also embraced by the present invention.

The compound (1) of the present invention can be prepared, for example, in accordance with the following reaction processes A or B.

[Process A]

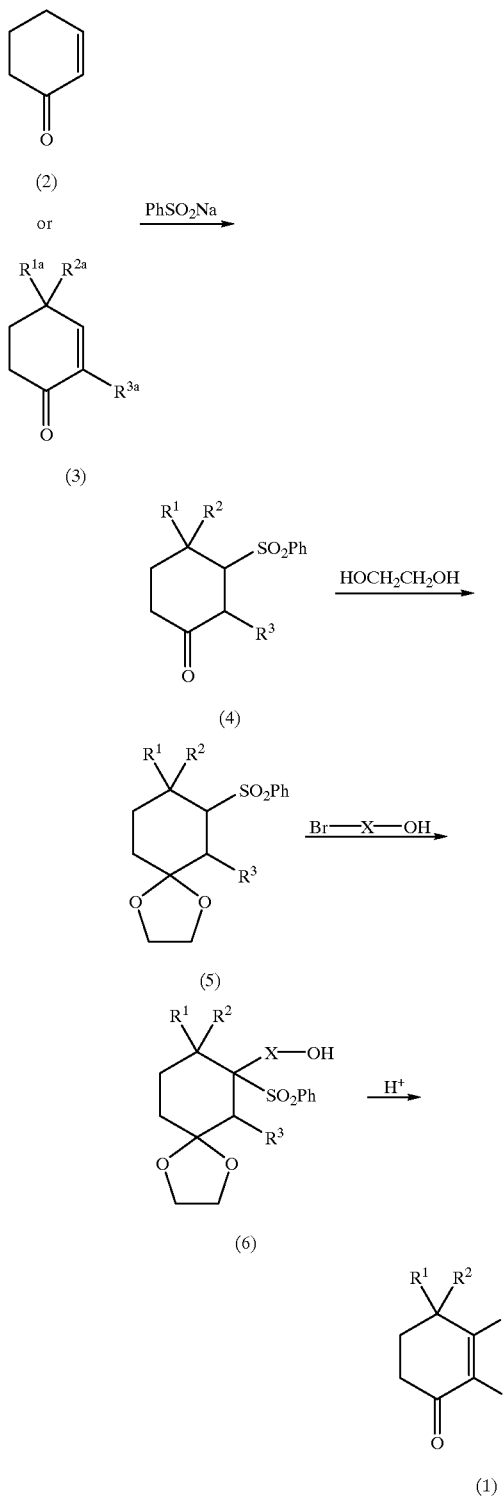

wherein $R^{1a}$, $R^{2a}$ and $R^{3a}$ each independently represents a hydrogen atom or a methyl group, with the proviso that at least one of them represents a methyl group, Ph represents a phenyl group and R1, R2 and R3 have the same meanings as defined above.

Described specifically, the invention compound (1) can be obtained by reacting cyclohexenone (2) or methyl-substituted-2-cyclohexen-1-one (3) with a benzenesulfinic acid salt in the presence of an acid to obtain Compound (4), reacting the resulting Compound (4) with ethylene glycol to obtain its ketal derivative (5), reacting the resulting derivative (5) with a ω-halogenoalkanol or ω-halogenoalkenol to obtain Compound (6), followed by subjecting Compound (6) to an acid treatment to eliminate the protective group.

The methyl-substituted-2-cyclohexen-1-one (3) used here as a raw material is available by reacting methyl-substituted cyclohexanone with a trialkylsilyl halide in the presence of butyl lithium, followed by oxidation in the presence of a palladium catalyst.

In the above reaction, the reaction between cyclohexanone (2) or methyl-substituted-2-cyclohexen-1-one (3) and a benzenesulfinic acid salt, for example, benzenesulfinic acid sodium is preferably effected in the presence of an acid such as hydrochloric acid, sulfuric acid or phosphoric acid at 0 to 100° C. for 5 to 40 hours.

The reaction between Compound (4) and ethylene glycol is preferably carried out in the presence of a condensing agent such as paratoluenesulfonic anhydride at 50 to 120° C. for 1 to 10 hours.

As a ω-halogenoalkanol to be reacted with the ketal derivative (5), a ω-bromoalkanol is preferred. It is desirable that the reaction between the ketal derivative (5) and a ω-bromoalkanol be carried out in the presence of a metal compound such as butyl lithium under low-temperature conditions.

The elimination of the phenylsulfonyl and ketal-protective groups from Compound (6) is preferably effected by reacting Compound (6) with an acid such as paratoluenesulfonic acid.

[Process B]

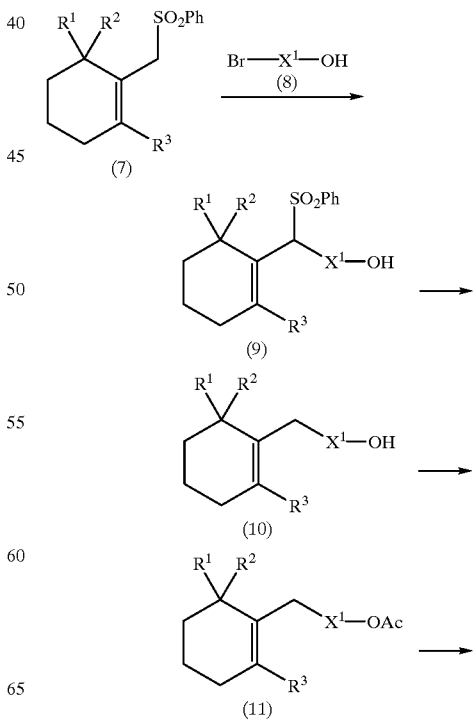

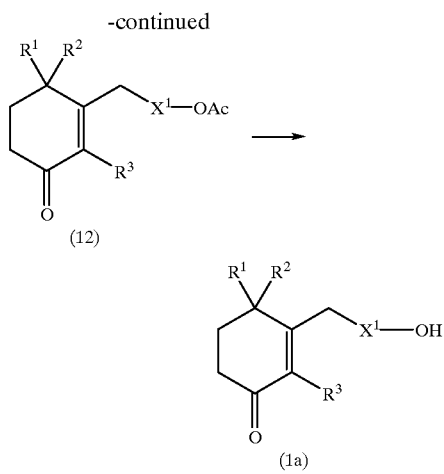

wherein X1 represents $C_{9-17}$ alkylene group or $C_{9-17}$ alkenylene group, Ac represents an acyl group, $R^1$, $R^2$, $R^3$ and Ph have the same meanings as defined above.

Described specifically, compound (7) (obtained, for instance, through the method described in *Synthesis*, 1996, November) is reacted with ω-bromoalcohol to obtain compound (9), subsequently the phenylsulphonyl group of the resulting compound being eliminated to give compound (10), followed by protection of the hydroxy group of compound (10) to yield compound (11). The resulting compound is subsequently oxidized to obtain compound (12), and the hydroxy-protective group of the resulting compound is then eliminated to obtain compound (12).

The reaction between compound (7) and compound (8) is preferably carried out at low temperatures in the presence of a metal compound such as butyl lithium.

The elimination of the phenylsulphonyl group from compound (9) may be conducted by reacting the compound and a phosphate in the presence of sodium amalgam.

As a hydroxy-protective group of compound (10), the acetyl group is preferred, the protection reaction being preferably performed, for example, by reacting compound (10) and acetic anhydride.

The oxidation reaction of compound (11) may preferably be performed by reacting the compound and an alkyl hydroperoxide such as t-butyl hydroperoxide in the presence of a metal compound such as ruthenium trichloride.

The elimination reaction of the protective group of compound (12) is preferably performed by hydrolyzing the compound in the presence of a base such as potassium carbonate.

Since the invention compound (1) so obtained has excellent neurite growth stimulating effects and is capable of passing through the blood-brain barrier owing to its low molecular weight, it is useful as a preventive and/or therapeutic for diseases caused by neural degeneration and defluxion, for example, dementia typified by Alzheimer's disease.

The medicament according to the present invention can be administered either through an oral route or a parenteral (such as intramuscular, subcutaneous, intravenous or suppository) route. Also, the medicament can be administered in the form of a composition comprising compound (1) and a pharmaceutically acceptable carrier.

Oral preparations can be formulated into tablets, covered tablets, granules, capsules, solutions, syrups, elixirs, oil or aqueous suspensions in a manner known per se in the art after the addition of an excipient and if necessary a binder, a disintegrator, a lubricant, a colorant and/or a corrigent. Examples of the excipient include lactose, corn starch, sucrose, glucose, sorbitol and crystalline cellulose. Examples of the binder include polyvinyl alcohol, polyvinyl ether, ethyl cellulose, methyl cellulose, gum arabic, tragacanth, gelatin, shellac, hydroxypropyl cellulose, hydroxypropyl starch and polyvinyl pyrrolidone.

Examples of the disintegrator include starch, agar, gelatin powder, crystalline cellulose, calcium carbonate, sodium bicarbonate, calcium citrate, dextran and pectin; those of the lubricant include magnesium stearate, talc, polyethylene glycol, silica and hardened vegetable oil. As the colorant, pharmaceutically acceptable colorants can be used. Examples of the corrigent include cocoa powder, menthol, aromatic acid, peppermint oil, camphor and cinnamon powder. The tablet can also be used in the form of a coated tablet available by applying sugar coating, gelatin coating or the like to granules as needed.

Injections, more specifically, subcutaneous, intramuscular and intravenous injections are formulated in a manner known per se in the art by adding a pH regulator, buffer, stabilizer and/or preservative as needed. It is also possible to fill the injection solution in a vial or the like and lyophilize it into a solid preparation which is reconstituted immediately before use. One dose is filled in a vial or alternatively, multiple doses are filled in one vial.

For human adult, the dose of the medicament according to the present invention falls within a range of from 0.01 to 1000 mg/day, with a range of from 0.1 to 100 mg/day being preferred. For animals, on the other hand, the dose falls within a range of from 0.01 to 1000 mg. preferably 0.1 to 100 mg per kg of the animal to be treated. This daily dose is administered once a day or in 2 to 4 portions a day.

EXAMPLES

The present invention will hereinafter be described by examples, but it should however be borne in mind that the present invention is not limited to or by these examples.

Example 1

(1) Benzenesulfinic acid sodium salt (10.25 g) was added to a solution containing 5 ml of cyclohexenone and 30 ml of water, followed by the dropwise addition of 60 ml of 1N hydrochloric acid. The reaction mixture was stirred at room temperature for 24 hours. The crystals so precipitated were filtered and then washed with water, isopropanol and cold ethyl ether. After recrystallization from isopropanol, 5.74 g of 3-(phenylsulfonyl)-cyclohexan-1-one were obtained in the form of white crystals. Yield: 97%

3-(Phenylsulfonyl)-cyclohexan-1-one

Molecular weight: 238 ($C_{12}H_{14}O_3S$)

Melting point: 83 to 85° C.

TLC: (hexane-AcOEt: 6-4) Rf=0.2

$^1$H NMR (200 MHz, CDCl$_3$), δ: 1.53–1.77 (m,2H,H-5); 2.1–2.45 (m, 4H,H-4,6); 2.6 (d,J=9.1 Hz, 2H,H-2); 3.2–3.4 (m,1H,H-3); 7.5–7.7 (m,3H,H ar.-3',4'); 7.8–7.9 (m,2H,H ar.-2').

$^{13}$C NMR (50 MHz, CDCl$_3$), δ: 23.2(C-5*); 23.5(C-4*) ;40.1(C-6°); 40.2(C-2°); 62.1(C-3); 128.8(C ar.-2'); 129.3(C ar.-3'); 134(C ar.-4'); 136.5(C ar.-1'); 206.2(C-1).

IR(KBr):3053,2966,2926,1708,1582,1450,1304,1288, 1228,119 8,1159,1138,1084,1062,912,765,728,693,661, 605,540.

UV(acetonitrile): λmax:222 nm(ε3740), λ:258(ε640) ,264(ε905),271(ε777).

MS(EI):238.1(M+,0.3); 143(PhSO$_2$H$_2$,0.2); 141(PhSO$_2$, 0.3); 125(PhSO,0.4); 120.1((CH$_2$)$_4$SO$_2$,0.4); 110(PhSH,0.3) ;97 (M—PhSO$_2$,0.3); 125(PhSO,0.4); 120.1 ((CH$_2$)$_4$SO$_2$, 0.4); 110 (PhSH,0.3)97(M—PhSO$_2$,100); 96(cyclohexene, 17); 77(Ph,19); 69.1((CH$_2$—)$_3$—CH=CH$_2$,63.2); 55.1 ((CH$_2$—)$_2$—CH=CH$_2$,22).

Analysis (%):calculated C,60.5;H,5.9;found C,60.4;H, 5.7.

(2) To a solution of 5.3 g of 3-(phenylsulfonyl)-cyclohexan-1-one in 60 ml of benzene, were added 0.3 ml of 1,2-ethanediol and 0.2 g of anhydrous paratoluenesulfonic acid. The reaction mixture was heated under reflux for 4 hours. After the reaction, a 2M aqueous sodium bicarbonate solution was added and the resulting mixture was extracted with ethyl acetate three times. The combined organic layers were washed with saturated saline and then, dried over magnesium sulfate. The solvent was distilled off under reduced pressure. The residue was recrystallized from ethyl ether, whereby 6.1 g of 1,1-(ethylenedioxy)-3-(phenylsulfonyl)-cyclohexane were obtained in the form of white crystals. Yield: 97%

1,1-(Ethylenedioxy)-3-(phenylsulfonyl)-cyclohexane

Molecular weight: 282 (C$_{14}$H$_{18}$O$_4$S)

Melting point: 93 to 95° C.

TLC: (hexane-AcOEt: 6-4) Rf=0.26

$^1$H NMR (200 MHz, CDCl$_3$), δ: 1.3–1.6 (m,3H,H-5,4a); 1.61(t,J=12.5 Hz,1H,H-2a); 1.65–1.73(m,1H,H4c) ;1.75–2.05(m,2H,H6);2.12(ddt,J$_{gem}$=12.5 Hz,$^3$J=3.5 Hz,$^4$J= 2.5 Hz,1H,H-2c); 3.21(tt,$^3$J=12.5 Hz,$^3$J=3.5 Hz,1H,H-3); 3.84–3.99 (m,4H, O—CH$_2$—CH$_2$—O); 7.5–7.7(m,3H,H ar.-3',4'); 7.8–7.9(m,2H,H ar.-2').

$^{13}$C NMR (50 MHz, CDCl$_3$), δ: 21.8(C-5); 24.5(C-4); 33.9(C-2*); 34.1(C-6*); 61.3(C-3); 64.4(O—CH$_2$—CH$_2$—O); 107.9(C-1); 128.9(C ar.-2'°); 129(C ar.-3'°); 133.6(C ar.-4'); 136.9(C ar.-1').

IR(KBr):3060,2968,2938,2894,1583,1448,1301,1267, 1158,114 4,1082,1023,939,916,838,749,718,689.

UV(acetonitrile):λmax:222 nm( ε4970),λ:258( ε710),264 (ε1010),271(ε861).

MS(Cl,NH$_3$) :300.2(MNH$_4$+,100); 283.1(MH+,27);256.1 (8);141.1(M—SO$_2$Ph,83).

Analysis (%):calculated C,59.82;H,6.32;found C,59.6;H, 6.4.

(3) A solution of n-butyl lithium (2 ml) was added dropwise to a solution of 565 mg of 1,1-(ethylenedioxy)-3-(phenylsulfonyl)-cyclohexane and 4 mg of triphenyl-methane in 5 ml of THF at −78° C. under an argon gas stream. After stirring for 10 minutes, the reaction was effected at room temperature for 1 hour. HMPT (1 ml) was added. The solution was stirred at room temperature for 1 hour after recooling to −78° C. A solution of 159 mg of 10-bromo-1-decanol in 2 ml of THF was added dropwise to the reaction mixture.

After reaction at −20° C. for 2 hours, the reaction mixture was poured into a saturated solution of ammonium chloride. The resulting mixture was extracted with ethyl ether. The organic layer was washed with water and saturated saline and then, dried over anhydrous magnesium sulfate. The solvent was distilled off under reduced pressure. The residue was purified by chromatography on a silica gel column while using hexane-ethyl acetate, whereby 265 mg of 1,1-(ethylenedioxy)-3-(10-hydroxydecyl)-3-(phenylsulfonyl)-cyclohexane were obtained in the form of a colorless oil. Yield: 90%

1,1-(Ethylenedioxy)-3-(10-hydroxydecyl)-3-(phenylsulfonyl)-cyclohexane

Molecular weight: 438 (C$_{24}$H$_{38}$O$_5$S)

TLC: (hexane-AcOEt: 6-4) Rf=0.14

$^1$ H NMR (200 MHz, CDCl$_3$)$_3$), δ: 1.26 (s large,14H,H-8 a H-14);1.57(q large,$^3$J=6.5 Hz,2H,H-15);1.6–1.94(m,8H, H-4,5,6,7);1.98(s,2H,H-2);3.64 (t,J=6.5 Hz,2H,H-16) ;3.86–3.92(m,4H,O—CH$_2$—CH$_2$—O);7.5–7.7 (m,3H,H ar.-3',4');7.81–7.87 (m,2H,H ar.-2').

$^{13}$C NMR (50 MHz, CDCl$_3$), δ: 19(C-5);23.8(C-14);25.7 (C-7);28.4(C-4);29.5(C-10 a C-13);30.2(C-8);30.5(C-9) ;32.7(C-15); 34.5(C-6);35.7(C-2);62.9(C-16); 63.8,64.8 (O—CH$_2$—CH$_2$—O);67.4(C-3);108.5(C-1);128.7(C ar.-3'*);130.3(C ar.-2'*);133.5(C ar.-4');135.8(C ar.-1').

IR(NaCl):3510,3063,2926,2853,1585,1447,1286,1140, 1096,10 83,723,693.

UV(acetonitrile) :λmax:218 nm( ε8600), λ:258( ε1050), 265(ε1300) ,271( ε1150).

MS(IC-NH$_3$): 456.3(MNH$_4$+,36);439.2(MH+,3.5);299.3 (MH$_2$—SO$_2$Ph,33);297.2(M—SO$_2$Ph,100);141(SO$_2$Ph,10) ;98.9(C$_6$H$_{11}$O, 28).

(4) Paratoluenesulfonic acid (20 mg) was added to a solution of 193 mg of 1,1-(ethylenedioxy)-3-(10-hydroxydecyl)-3-(phenylsulfonyl)-cyclohexane in 3 ml of chloroform and 0.6 ml of acetone. To the resulting mixture was added 10 ml of a saturated aqueous solution of sodium bicarbonate, followed by extraction with dichloromethane. The organic layer was washed with saturated saline and dried over magnesium sulfate. The solvent was distilled off under reduced pressure. The residue was purified by chromatography on a silica gel column using hexane-ethyl acetate, whereby 86 mg of 3-(10-hydroxydecyl)-2-cyclohexen-1-one were obtained in the form of a colorless oil. Yield: 77%

3-(10-Hydroxydecyl)-2-cyclohexen-1-one

Molecular weight 252 (C$_{16}$H$_{28}$O$_2$)

TLC: (hexane-AcOEt: 6-4) Rf=0.33

$^1$H NMR (200 MHz, CDCl$_3$), δ: 1.28 (s large,14H,H-8 a H-14);1.44–1.59(m,2H,H-15);1.97(q.J=6.4 Hz,2H,H-5) ;2.1–2.4(m,6H,H-4,6,7);3.64 (t,J=6.4 Hz,2H,H-16);5.87 (s,1H,H-2).

$^3$C NMR (50 MHz, CDCl$_3$), δ: 22.6(C-5);25.6(C-14);26.8 (C-4);29.3(C-8 to C-13):32.6(C-15);37.2(C-7);37.9(C-6) ;62.7(C-16);125.5(C-2);166.9(C-3);200.1(C-1).

IR(NaCl):3446,3058,2926,2854,1665,1624,1446,1301, 1152,11 25,1078,728,693.

UV(acetonitrile): λmax:232 nm( ε16050).

MS(EI):252.1(M+,9);222.1(8);124(12);123(C$_8$H$_{11}$O,93) ;110(100);97(C$_6$H$_9$O,65);95(C$_6$H$_7$O,22);82(64);81(13);79 (12); 66.9(26); 55(23).

Analysis (%):calculated C,79.14;H,11.18; found: C,75.8;H,10.9.

Example 2

In a similar manner to Example 1, 3-(11-hydroxy-undecyl)-2-cyclohexen-1-one was obtained.

Molecular weight: 266 (C$_{17}$H$_{30}$O$_2$)

TLC: (hexane-AcOEt: 6-4) Rf=0.2

Melting point: 34 to 35° C.

MS(EI):266.1(M+,9); 248.1(M—H$_2$O,2); 236.1(8); 124 (11); 123(C$_8$H$_{11}$O,83);109.9(100);97(56);95(C$_6$H$_7$O,25);82 (51); 81(13);79(12);69(7);66.9(23);55(21).

Analysis (%): calculated C,76.64;H,11.35; found:C,76.4; H,11.6.

Example 3

In a similar manner to example 1, 3-(12-hydroxy-dodecyl)-2-cyclohexen-1-one was obtained.

Molecular weight: 280 ($C_{18}H_{32}O_2$)
TLC: (hexane-AcOEt: 6-4) Rf=0.24
Melting point: 35 to 36° C.
MS(EI):280.3($M^+$,12); 262.1(M—$H_2O$,3); 250.1(7); 150.9($C_{10}H_{25}O$,5); 136.9($C_9H_{13}O$,4); 124(10); 123 ($C_8H_{11}O$,84); 110(100); 97(51); 95($C_6H_7O$,22); 82(46); 81(10); 78.9(10); 66.9(20); 55(22).
Analysis (%): calculated C,77.07;H,11.50; found:C;77.1 H;11.5.

Example 4

In a similar manner to Example 1, 3-(13-hydroxy-tridecyl)-2-cyclohexen-1-one was obtained.

Molecular weight: 294 ($C_{19}H_{34}O_2$)
TLC: (hexane-AcOEt: 6-4) Rf=0.26
Melting point: 42 to 43° C.
MS(EI):294.2($M^+$,8); 276.1(M—$H_2O$,2); 264.1(5); 151 ($C_{10}H_{15}O$,5); 136.9($C_9H_{13}O$,4); 124(9); 123($C_8H_{11}O$,77); 111(8); 109.9(100); 97(46); 95($C_6H_7O$,20); 82(36); 81.1 (10); 78.9(8); 66.9(18); 55(21).
Analysis (%): calculated C,77.50; H,11.64; found:C,77.4; H,11.5.

Example 5

In a similar manner to Example 1, 3-(14-hydroxy-tetradecyl)-2-cyclohexen-1-one was obtained.

Molecular weight: 308 ($C_{20}H_{36}O_2$)
TLC: (hexane-AcOEt: 6-4) Rf=0.28
Melting point: 44 to 45° C.
MS(EI):308.1($M^+$,10); 290.3(M—$H_2O$,3); 278.4(6); 150.9($C_{10}H_{15}O$,5); 137($C_9H_{13}O$,3); 124(8); 123($C_8H_{11}O$, 77); 111(8); 109.9(100); 97(44); 95($C_6H_7O$,19); 82(30); 81.1(8); 78.9(7); 66.9(18); 55(20).
Analysis (%): calculated C,77.87; H,11.76; found:C,77.6; H,11.4.

Example 6

(1) A 1.4 M n-butyl lithium solution (35.4 ml) was added dropwise to a solution of 7 ml of N,N-diisopropylamine in 20 ml of THF at −78° C. The resulting mixture was stirred at 0° C. for 30 min. Four ml of 4-methylcyclohexan-1-one in 10 ml of THF at −78° C. was added dropwise to the LDA solution. After stirring at −78° C. for 1 hour, 6.5 ml of trimethylsilyl chloride were added to the reaction mixture. The resulting mixture was stirred at room temperature for 1 hour and then poured into an aqueous solution of sodium bicarbonate, followed by extraction with ethyl ether. The organic layer was washed with saturated saline and dried over magnesium sulfate. The solvent was distilled off under reduced pressure. The residue was purified by distillation under reduced pressure, whereby 5.83 g of 4-methyl-1-(trimethylsilyloxy)-1-cyclohexene were obtained. Yield: 96%

4-Methyl-1-(trimethylsilyloxy)-1-cyclohexene

Molecular weight: 184 ($C_{10}H_{20}OSi$)
TLC: (hexane-AcOEt: 8-2) Rf=0.8
$^1$H NMR (200 MHz, $CDCl_3$), δ: 0.17 (s,9H,Si—$(CH_3)_3$); 0.94(d.J=6.2 Hz,3H,H-7);1.2–1.43(m,1H,H-4);1.57–1.76 (m,3H,H-3.6); 1.88–2.14 (m,3H,H-5); 4.8–4.83 (m,1H,H-2).
$^{13}$C NMR (50 MHz, $CDCl_3$), δ: 0.3(Si—$(CH_3)_3$);21.2(C-7);28.3(C-4);29.6(C-5);31.3(C-6);32.3(C-3);103.5(C-2) ;150.1(C-1).
IR(NaCl):3052,3021,2954,2926,1670,1457,1371,1252, 1190,10 46,892,844.

(2) A catalytic amount of palladium (II) acetate was added to a solution of 3.53 g of 4-methyl-1-(trimethylsilyloxy)-1-cyclohexene in 70 ml of DMSO, followed by stirring while introducing oxygen for 6 hours. After the addition of water at 0° C., the reaction mixture was filtered over celite and then extracted with ethyl ether. The solvent was distilled off under reduced pressure and the residue was dissolved in hexane-water. The resulting solution was extracted with hexane. The hexane layer was washed with saturated saline and dried over magnesium sulfate. The solvent was distilled off under reduced pressure, whereby 4-methyl-2-cyclohexen-1-one was obtained in the form of an oil. Yield: 72%

4-Methyl-2-cyclohexen-1-one

Molecular weight: 110 ($C_7H_{10}O$)
TLC: (hexane-AcOEt: 8-2) Rf=0.35
$^1$H NMR (200 MHz, $CDCl_3$), δ: 1.15 (d,J=7.1 Hz,3H,H-7); 1.56–1.76(m,1H,H-5a);2.1(dqa,$J_{emg}$=13.3 Hz, $^3$J=4.9 Hz,1H,H-5e);2.26–2.48(m,2H,H-6);2.49–2.62 (m,1H,H-4); 5.94 (dd, $^3$J=10.1 Hz, $^4$J=2.5 Hz,1H,H-2);6.79 (ddd, $^3$J=10.1 Hz, $^3$J=2.7, $^4$J=1.5 Hz,1H,H-3).
$^{13}$C NMR (50 MHz, $CDCl_3$), δ: 20.1(C-7);29.6(C-5);30.9 (C-4);36.8(C-6);128.4(C-2);156.2(C-3);199.7(C-1).
IR(NaCl):3025, 2958, 2932, 1683, 1617, 1458, 1391, 1375, 1251, 1094, 1053, 1016, 828, 750.

(3) Benzenesulfinic acid sodium salt (3.0 g) was added to a solution containing 1.52 g of 4-methyl-2-cyclohexen-1-one and 9 ml of water. 1N Hydrochloric acid (18 ml) was added dropwise to the resulting solution. After stirring at room temperature for 24 hours, the crystals so precipitated were filtered and washed with water, isopropanol and cold ethyl ether. After recrystallization from isopropanol, 4-methyl-3-(phenylsulfonyl)-cyclohexan-1-one was obtained in the form of white crystals. Yield: 72%

4-Methyl-3-(phenylsulfonyl)-cyclohexan-1-one

Molecular weight: 252 ($C_{13}H_{16}O_3S$)
Melting point: 71 to 74° C.
TLC* (hexane-AcOEt: 6-4) Rf=0.2
$^1$H NMR (200 MHz, $CDCl_3$),
trans: δ: 1.32 (d, J=6.9 Hz,3H,H-7); 1.5–1.7 (m, 1H,H-5); 2.15–2.3(m,1H,H-5); 2.35–2.5 (m,3H,H-4.6) ;2.55–2.68 (m,2H,H-2); 3.17(ddd,J=8 Hz,J=6.6 Hz,J= 6.4 Hz,1H,H-3); 7.52–7.72(m,3H,H ar.-3',4'); 7.83–7.9 (m,2H,H ar.-2').
cis: δ: 1.44 (d, J=7.1 Hz,3H,H-7); 1.75–1.9 (m, 1H,H-5); 1.95–2.1(m,1H,H-5); 2.35–2.5 (m,3H,H-4.6);2.73–2.9 (m,2H,H-2); 3.34(dt,J=12.9 Hz,J=4 Hz,1H,H-3); 7.52–7.72(m,3H,H ar.-3',4'); 7.83–7.9(m,2H,H ar.-2').
$^{13}$C NMR (50 MHz, $CDCl_3$),
trans: δ: 20.3(C-7); 28.5(C-4);30.4(C-5); 37.9(C-6*); 38.6(C-2*); 66.3(C-3); 128.6(C ar.-$2^{10}$); 129.1(C ar.-$3^{10}$); 133.9(C ar.-4'); 137.2(C ar.-1');206.1(C-1).
cis: δ: 13(C-7); 27.2(C-4);31.1(C-5); 35.9(C-6*); 36.9(C-2*); 64.6(C-3); 128.3(C ar.-$2^{10}$); 129.1(C ar.-$3^{10}$);

133.9(C ar.-4'); 138(C ar.-1');206.6(C-1). MS(El):111.1 (M—SO$_2$Ph,88); 110.1(27); 83.15(32); 77.1(29); 69.1 (36); 55.2(100).

(4) To a solution of 2.45 g of 4-methyl-3-(phenylsulfonyl)-cyclohexan-1-one in 40 ml of benzene, were added 0.7 ml of 1,2-ethanediol and 0.2 g of anhydrous paratoluenesulfonic acid. The resulting mixture was heated under reflux for 4 hours. After the reaction, a 2M aqueous sodium bicarbonate solution was added and the resulting mixture was extracted with ethyl acetate three times. The combined organic layers were washed with saturated saline, and dried over magnesium sulfate. The solvent was then distilled off under reduced pressure. The residue was recrystallized from ethyl ether, whereby 1,1-(ethylenedioxy)-4-methyl-3-(phenylsulfonyl)-cyclohexane was obtained in the form of white crystals. Yield: 97%

Molecular weight: 296 (C$_{15}$H$_{20}$O$_4$S)

Melting point: 105 to 106° C.

TLC: (hexane-AcOEt: 6-4) Rf=0.3

$^1$H NMR (200 MHz, CDCl$_3$), trans: δ: 1.23 (d, J=6.1 Hz,3H,H-7); 1.37–1.77 (m, 6H,H-2a,4,5,6); 1.84(ddd,J$_{gem}$=12.9 Hz,$^3$J=3.7 Hz,$^4$J=2.7 Hz,1H,H-2e); 3.02 (ddd,$^3$J=13 Hz,$^3$J=10.3 Hz, $^3$J=3.7 Hz,1H,H-3);3.71–3.91(m,4H,O—CH$_2$—CH$_2$—O); 7.48–7.67(m,3H,H ar.-3',4'); 7.8–7.88(m,2H,H ar.-2').

cis: δ: 1.18 (d, J=6.9 Hz,3H,H-7); 1.37–1.77 (m,4H,H-5.6); 7.84(ddd,J$_{gem}$=13 Hz,$^3$J=3.7 Hz,$^4$J=2.7 Hz,1H,H-2e); 2.02 (t,J=13 Hz,1H,H-2a);2.30–2.45 (m,1H,H-4); 3.29(dt,$^3$J=13 Hz,$^3$J=3.7 Hz,1H,H-3); 3.71–3.91(m,4H, O—CH$_2$—CH$_2$—O); 7.48–7.67(m,3H,H ar.-3',4'); 7.8–7.88(m,2H,H ar.-2').

$^{13}$C NMR (50 MHz, CDCl$_3$), trans: δ: 20.4(C-7); 31.9(C-4);32.6(C-5); 34.1(C-6); 35.8 (C-2); 64.4(CH$_2$—O); 66.8(C-3); 107.9(C-1); 128.6(C ar.-3'*); 129(C ar.-2'*);133.5(C ar.-4');138(C ar.-1').

-cis: δ: 12.4(C-7); 26.7(C-4);29.2(C-5.6); 32(C-2); 64.1 (C-3); 64.4(CH$_2$—O); 108.2(C-1); 128.3(C ar.-2',3'); 133.5(C ar.-4'); 138.5(C ar.-1').

IR(KBr): 3060, 2968, 2938, 1583, 1448, 1301, 1267, 1158, 1144, 1082, 1023, 939, 916, 838, 749, 718, 689.

Analysis (%): calculated C$_{15}$H$_{20}$O$_4$S(296.4)C,60.79; H,6.8; found: C,60.5; H,6.9.

(5) A solution of n-butyl lithium (1.8 ml) was added dropwise to a solution of 560 mg of 1,1-(ethylenedioxy)-4-methyl-3-(phenylsulfonyl)-cyclohexane and 4 mg of triphenylmethane in 5 ml of THF under an argon stream at −78° C. The resulting mixture was stirred for 10 minutes and then reacted at room temperature for 1 hour. HMPA (1 ml) was added and the resulting mixture was recooled to −78° C., followed by the dropwise addition of a solution of 166 mg of 10-bromo-1-decanol in 2 ml of THF. After stirring the reaction at −20° C. for 2 hours, the reaction mixture was poured into a saturated solution of ammonium chloride. The resulting mixture was extracted with ethyl ether. The organic layer was washed with water and saturated saline and then, dried over magnesium sulfate. The solvent was distilled off under reduced pressure. The residue was purified by chromatography on a silica gel column while using hexane-ethyl acetate, whereby 1,1-(ethylenedioxy)-3-(10-hydroxydecyl)-4-methyl-3-(phenylsulfonyl)-cyclohexane was obtained in the form of a colorless oil. Yield: 97%

1-1-(Ethylenedioxy)-3-(10-hydroxydecyl)-4-methyl-3-(phenylsulfonyl)-cyclohexane

Molecular weight: 452 (C$_{25}$H$_{40}$O$_5$S)

TLC: (hexane-AcOEt: 6-4) Rf=0.14

$^1$H NMR (200 MHz, CDCl$_3$), δ: 1.13 (d,j=6 Hz,3H,H-17); 1.28(s large,12H,H-9a,H-14); 1.43–1.6(m,9H,H-4,5,6,7,8, 15); 1.67(m,1H,H-2); 1.89(dd, J$_{gem}$=12.5 Hz,J=3.5 Hz,1H, H-6e); 2.14(t large,J=12.5 Hz,1H,H-6a); 2.43(dd, J$_{gem}$=13.8 Hz,$^4$J=2.5 Hz,1H,H-2); 3.63(t,J=6.5 Hz,2H,H-16); 3.83–3.97(m,4H,O—CH$_2$—CH$_2$—O);7.49–7.68(m,3H,H ar.-3',4'); 7.8–7.88(m,2H,H ar. -2').

$^{13}$C NMR (50 MHz, CDCl$_3$), δ: 16.1(C-17); 24.4(C-14); 25.6(C-5*); 25.8(C-7*); 29.5(C-9 a C-13); 30.3(C-8); 32.7 (C-15); 34.9(C-6); 35.5(C-4); 36.2(C-2); 32.8(C-16);63.9, 65.1(O—CH$_2$—CH$_2$—O); 71.2(C-3); 108.4(C-1); 128.7(C ar.-3'); 130.1(C ar.-2'); 133.3(C ar.-4'); 136.8(C ar.-1').

IR(KBr):3510, 3063, 2926, 2853, 1584, 1286, 1140, 1096, 1083.

MS(Cl—NH$_3$): 470.3(MNH$_4$$^+$,2); 313.3(MH$_2$—SO$_2$Ph, 23); 312.3(MH—SO$_2$Ph,19); 311.2(M—SO$_2$Ph,100); 255.1 (19); 155(5); 99(59); 81(5); 78(9).

(6) Paratoluenesulfonic acid (20 m) was added to a solution of 235 mg of 1,1-(ethylenedioxy)-3-(10-hydroxydecyl)-4-methyl-3-(phenylsulfonyl)-cyclohexane in 20 ml of chloroform and 4 ml of acetone. The resulting mixture was reacted at 50° C. for 24 hours. To the reaction mixture were added 10 ml of a saturated aqueous solution of sodium bicarbonate, followed by extraction with dichloromethane. The organic layer was washed with saturated saline and dried over magnesium sulfate. The solvent was distilled off under reduced pressure. The residue was purified by chromatography on a silica gel column while using hexane-ethyl acetate, whereby 3-(10-hydroxydecyl)-4-methyl-2-cyclohexen-1-one was obtained in the form of a colorless oil. Yield: 75%

3-(10-Hydroxydecyl)-4-methyl-2-cyclohexen-1-one

Molecular weight: 266 (C$_{17}$H$_{30}$O$_2$)

CCM: (hexane-AcOET: 6-4) Rf=0.2

$^1$H NMR (200 MHz, CDCl$_3$), δ: 1.18 (d,J=7.1 Hz,3H,H-17); 1.27(s large,12H,H-9 to H-14); 1.40–1.57(m,4H,H-8, 15); 1.76(dqa,J$_{gem}$=13.3 Hz,J=5.8 Hz,1H,H-5e); 2.01–2.13 (m,1H,H-5a); 2.15–2.26 (m,2H,H-7); 2.28–2.56(m,3H,H-4, 6); 3.63(t,J=6.4 Hz,2H,H-16); 5.8(s large,1H,H-2).

$^{13}$C NMR (50 MHz, CDCl$_3$), δ: 17.6(C-17); 25.6(C-14); 26.9(C-5); 29.2(C-9 a C-13); 30(C-8); 32.6(C-15); 32.8(C-4); 34(C-7); 35.4(C-6); 62.6(C-16); 124.6(C-2); 170.7(C-3); 199.7(C-1).

IR(KBr):3450, 3058, 2926, 2854, 1665, 1624, 1055, 1043.

UV(acetonitrile): λmax:228 nm(ε10840).

MS(EI):266.1(M$^+$,31);248.1(M—H$_2$O,6); 236.1(21); 165 (C$_{11}$H$_{17}$O,8); 151(C$_{10}$H$_{15}$O,5); 138(14); 137(C$_9$H$_{13}$O,100); 123.9(98); 111(85); 110(21); 109(C$_7$H$_9$O,38); 96(56); 95(29); 82.1(11); 81(29); 78.9(15); 69(10); 67(29); 55(38).

Analysis (%): calculated C$_{17}$H$_{30}$O$_2$(266.4) C,76.64; H,11.35; found C,76.5;H,11.5.

Example 7

In a similar manner to Example 6, 3-(11-hydroxyundecyl)-4-methyl-2-cyclohexen-1-one was obtained.

Molecular weight: 280 (C$_{18}$H$_{32}$O$_2$)

TLC: (hexane-AcOET: 6-4) Rf=0.21

MS(EI):280.1(M$^+$,25);262.1(M—H$_2$O,7); 250.1(21); 165 (C$_{11}$H$_{17}$O,7); 151(C$_{10}$H$_{15}$O,5); 138.1(13); 137(C$_9$H$_{13}$O, 100); 123.9(94); 111(86); 110(20); 109(C$_7$H$_9$O,41); 96(46); 95.1(26); 82.1(10); 81(28); 78.9(15); 69(12); 67(28); 55(35).

Analysis (%): calculated C,77.09; H,11.50; found C,76.9;H,11.3.

Example 8

In a similar manner to Example 6, 3-(12-hydroxy-dodecyl)-4-methyl-2-cyclohexen-1-one was obtained.

Molecular weight: 294 ($C_{19}H_{34}O_2$)

TLC: (hexane-AcOET: 6-4) Rf=0.22

MS(EI):294.1($M^+$,29);276.1(M—$H_2O$,8); 364.1(21); 165 ($C_{11}H_{17}O$,7); 151($C_{10}H_{15}O$,4); 138.1(12); 137($C_9H_{13}O$, 100); 123.9(88); 111(73); 110(17); 109($C_7H_9O$,36); 96(37); 95.1(22); 82(9); 80.9(28); 78.9(13); 69(12); 67(25); 55(32).

Analysis (%): calculated C,77.50; H,11.64; found C,77.2; H,11.5.

Example 9

In a similar manner to Example 6, 3-(13-hydroxy-tridecyl)-4-methyl-2-cyclohexen-1-one was obtained.

Molecular weight: 308 ($C_{20}H_{36}O_2$)

TLC: (hexane-AcOET: 6-4) Rf=0.25

MS(EI):308.1($M^+$,31);290.1(M—$H_2O$,10); 278.1(21); 164.9($C_{11}H_{17}O$,9); 151($C_{10}H_{15}O$,4); 138.1(12); 137 ($C_9H_{13}O$,90); 123.9(100); 111(73); 110(17); 109($C_7H_9O$, 40); 96(33); 94.9(26); 81(25); 79(13); 69(14); 67(23); 55(37).

Analysis (%): calculated C,77.87; H,11.76; found C,77.6; H,11.5.

Example 10

In a similar manner to Example 6, 3-(14-hydroxy-tetradecyl)-4-methyl-2-cyclohexen-1-one was obtained.

Molecular weight: 322 ($C_{21}H_{38}O_2$)

TLC: (hexane-AcOET: 6-4) Rf=0.3

MS(EI):322.2($M^+$,37);304.1(M—$H_2O$,12); 292.1(21); 164.9($C_{11}H_{17}O$,9); 151($C_{10}H_{15}O$,4); 138.1(12); 137 ($C_9H_{13}O$,98); 123.9(100); 111(69); 110(17); 109($C_7H_9O$, 43); 96(30); 94.9(24); 81(24); 78.9(13); 69(15); 67(25); 55(37).

Analysis (%): calculated C,78.20; H,11.88; found C,78.6; H,11.9.

Example 11

(1) Benzenesulfinic acid sodium salt (5.98 g) was added to a solution containing 3 ml of 4,4-dimethyl-2-cyclohexen-1-one and 20 ml of water. Forty ml of 1N hydrochloric acid were added dropwise to the resulting mixture. The reaction mixture was stirred at room temperature for 24 hours. The crystals so precipitated were filtered and the solid, washed with water, isopropanol and cold ethyl ether. After recrystallization from isopropanol, 4,4-dimethyl-3-(phenylsulfonyl)-cyclohexan-1-one was obtained in the form of white crystals. Yield: 89%

4,4-Dimethyl-3-(phenylsulfonyl)-cyclohexan-1-one

Molecular weight: 206 ($C_{14}H_{18}O_3S$)

Melting point: 84 to 86° C.

TLC: (hexane-AcOET: 6-4) Rf=0.3

$^1$H NMR (200 MHz, $CDCl_3$), δ: 1.52 (s,6H,H7,8); 1.67 (ddd, $J_{gem}$=14 Hz ,$^3$J=12.3 Hz ,$^3$J=4.4 Hz,1H,H-5a); 1.85 (ddd,$J_{gem}$=14 Hz,$^3$J=6.2 Hz, $^3$J=4.4 Hz,1H,H-5e); 2.26(ddd, $J_{gem}$=15.5 Hz,$^3$J=4.6 Hz,$^4$J=2 Hz,1H,H-2e); 2.29(dtd,$J_{gem}$= 15.7 Hz,$^3$J=4.4 Hz,$^4$J=2 Hz,1H,H-6e); 2.51(dddd,$J_{gem}$=15.7 Hz,$^3$J=12.3 Hz,$^3$J=6.2 Hz,$^4$J=1 Hz,1H,H-6a); 2.75(ddd, $J_{gem}$=15.5 Hz,$^3$J=12.2 Hz,$^4$J=1 Hz,1H,H-2a); 3.18(dd,$^3$J= 12.2 Hz,$^3$J=4.6 Hz,1H,H-3); 7.52–7.7(m,3H,H ar.-3',4') ;7.82–7.88(m,2H,H ar.-2').

$^{13}$C NMR (50 MHz, $CDCl_3$), δ: 21.3(C-7); 30(C-8); 34.8(C-4); 37.1(C-6); 38.9(C-2); 40.8(C-5); 69(C-3); 128.4(C ar.-2'*); 129.3(C ar.-3'*); 133.8(C ar.-4'); 139.1(C ar.-1');207.1(C-1).

Analysis(%): calculated $C_{14}H_{18}O_3S$(266.4) C,63.13; H,6.8; found:C,63; H,6.6.

(2) To a solution obtained by dissolving 4.4 g of 4,4-dimethyl-3-(phenylsulfonyl) -cyclohexan-1-one in 45 ml of benzene, were added 1.1 nm of 1,2-ethanediol and 0.3 g of anhydrous paratoluenesulfonic acid. The resulting mixture was heated under reflux for 4 hours. After the reaction, a 2M aqueous sodium bicarbonate solution was added and the resulting mixture was extracted with ethyl acetate three times. The combined organic layers were washed with saturated saline and dried over magnesium sulfate. The solvent was distilled off under reduced pressure, followed by recrystallization from ethyl ether, whereby 4,4-dimethyl-1, 1-(ethylenedioxy)-3-(phenylsulfonyl)-cyclohexane was obtained in the form of white crystals. Yield: 84%

4,4-Dimethyl-1,1-(ethylenedioxy)-3-(phenylsulfonyl)-cyclohexane

Molecular weight: 310 ($C_{16}H_{22}O_4S$)

Melting point: 113 to 115° C.

TLC: (hexane-AcOET: 6-4) Rf=0.36

$^1$H NMR (200 MHz, $CDCl_3$), δ: 1.27 (s,3H,H-7); 1.34–1.41(m,1H,H-5); 1.37(s,3H,H-8); 1.45–1.78(m,4H,H-2e,5,6); 2.01(t,$^3$J=13.1 Hz,1H,H-2a); 3.15(dd,$^3$J=13.1 Hz,$^3$J=3.4 Hz,1H,H-3); 3.6–3.93(m,4H,O—$CH_2$—$CH_2$—O); 7.50–7.67(m,3H,H ar.-3',4'); 7.86–7.90(m,2H,H ar.-2').

$^3$C NMR (50 MHz, $CDCl_3$), δ: 20(C-7); 30.6(C-8); 30.8 (C-6); 32.5(C-2); 34.5(C-4); 40.8(C-5); 64(O—$\underline{C}H_2$—$CH_2O$); 64.3(O—$CH_2$—$\underline{C}H_2O$); 68.8(C-3);108.1(C-1);128.3(C ar.-2'*);129(C ar.-3'*);133.3(C ar.-4');139.9(C ar.-1').

Analysis(%): calculated C,61.91; H,7.14; found: C,62; H,7.1.

(3) A solution of n-butyl lithium (2.93 ml) was added dropwise to a solution of 930 mg of 4,4-dimethyl-1,1-(ethylenedioxy)-3-(phenylsulfonyl)-cyclohexane and 4 mg of triphenylmethane in 5 ml of THF at −78° C. under an argon stream. After stirring for 10 minutes, the mixture was reacted at room temperature for one hour. HMPA (1 ml) was added to the reaction mixture, followed by recooling to −78° C. A solution of 236 mg of 10-bromo-1-decanol in 2 ml of THF was added dropwise to the reaction mixture.

After the reaction at −20° C. for 2 hours, the reaction mixture was poured into a saturated solution of ammonium chloride. The resulting mixture was extracted with ethyl ether. The organic layer was washed with water and saturated saline, and dried over magnesium sulfate. The solvent was then distilled off under reduced pressure. The residue was purified by chromatography on a silica gel column while using hexane-ethyl acetate, whereby 4,4-dimethyl-1, 1-(ethylenedioxy)-3-(10-hydroxydecyl)-3-(phenylsulfonyl)-cyclohexane was obtained in the form a colorless oil. Yield: 94%

4,4-Dimethyl-1,1-(ethylenedioxy)-3-(10-hydroxydecyl)-3-(phenylsulfonyl)-cyclohexane Molecular weight: 466 ($C_{26}H_{45}O_5S$)

TLC: (hexane-AcOET: 6-4) Rf=0.15

$^1$H NMR (200 MHz, CDCl$_3$), δ: 1.17 (s,3H,H-17); 1.05–1.4(m,14H,H-8 to H-14); 1.42(s,3H,H-18); 1.49–1.64 (m,2H,H-15); 1.77–2(m,4H,H-2,6); 2.6(d,J$_{gem}$=14.3 Hz,1H, H-2); 3.65(t,J=6.3 Hz,2H,H-16); 3.77–3.96(m,4H,O—CH$_2$—CH$_2$—O); 7.47–7.66(m,3H,H ar.-3',4'); 7.83–7.88(m, 2H,H ar.-2').

$^{13}$C NMR (50 MHz, CDCl$_3$), δ: 24.1(C-14); 25.4(C-17, 18); 25.7(C-7); 29.5(C-10 to C-13); 30.2(C-8); 31.1(C-2*); 31.5(C-6*); 32.7(C-15); 33.3(C-9); 38.1(C-4); 38.6(C-5); 62.9(C-16);63.8,64.7(O—CH$_2$—CH$_2$—O); 75(C-3); 108.9 (C-1); 128.8(C ar.-2'); 129.8(C ar.-3'); 133.2(C ar.-4'); 140.7(C ar.-1').

IR(KBr):3474, 3064, 2925, 2853, 1590, 1464, 1447, 1297, 1135, 1078, 729, 692.

MS(Cl—NH$_3$): 484.3(MNH$_4^+$,12); 327.3(44); 326.3(22); 325.3(M—SO$_2$Ph,100); 282.2(5); 265.2(6); 255.2(5); 174.9 (8); 160(6); 99(17).

(4) Paratoluenesulfonic acid (20 mg) was added to a solution of 400 mg of 4,4-dimethyl-1,1-(ethylenedioxy)-3-(10-hydroxydecyl)-3-(phenylsulfonyl)-cyclohexane in 30 ml of chloroform and 6 ml of acetone. The resulting mixture was reacted at 50° C. for 24 hours. To the reaction mixture, were added 10 ml of a saturated sodium bicarbonate solution, followed by extraction with dichloromethane. The organic layer was washed with saturated saline and dried over magnesium sulfate. The solvent was then distilled off under reduced pressure. The residue was purified by chromatography on a silica gel column while using hexane-ethyl acetate, whereby 4,4-dimethyl-3-(10-hydroxydecyl)-2-cyclohexen-1-one was obtained in the form of a colorless oil. Yield: 78%

4,4-Dimethyl-3-(10-hydroxydecyl)-2-cyclohexen-1-one

Molecular weight: 280 ($C_{18}H_{32}O_2$)

TLC: (hexane-AcOET: 6-4) Rf=0.25

$^1$H NMR (200 MHz, CDCl$_3$), δ: 1.16 (s, 6H,H-17, 18); 1.30(s large,12H,H-9 to H-14); 1.42–1.63(m,4H,H-8,15); 1.85(t,J=6.6 Hz,2H,H-5); 2.19(t,J=7 Hz,2H,H-7); 2.44(t,J=6.6 Hz,2H,H-6); 3.64(t,J=6.4 Hz,2H,H-16); 5.79(s,1H,H-2).

$^{13}$C NMR (50 MHz, CDCl$_3$), δ: 25.7(C-14); 26.4(C-17, 18); 27.4(C-8); 29.4(C-9 a C-13); 31.9(C-7); 32.7(C-15); 34.2(C-6); 35.6(C-4); 37.9(C-5); 62.9(C-16); 124.2(C-2); 172.9(C-3); 199.6(C-1).

IR(NaCl):3425, 2928, 2853, 1660, 1610, 1464, 1412, 1366, 1330, 1276, 1245, 867.

UV(acetonitrile): λmax:232 nm(ε12120).

MS(EI):280(M$^+$,24);262.1(M—H$_2$O,4); 250.1(21); 224 (8); 196.1(6); 179(C$_{12}$H$_{19}$O,8); 152.1(12); 151(C$_{10}$H$_{15}$O, 100); 138(35); 125.1(34); 124.1(31); 123(39); 121(13); 110 (23); 109(27); 107(C$_7$H$_7$O,11);96(27); 95(36); 82(12); 81(21); 79(16); 69(15); 67(29); 55.1(33).

Analysis (%):calculated C,77.09; H,11.50; found C,76.3;H,11.4.

Example 12

In a similar manner to Example 11, 3-(11-hydroxyundecyl)-4,4-dimethyl-2-cyclohexen-1-one was obtained.

Molecular weight: 294 ($C_{19}H_{34}O_2$)

TLC: (hexane-AcOET: 6-4) Rf=0.25

MS(EI):294(M$^+$,14);276.1(M—H$_2$O,4); 264.1(23); 249.1 (5); 238.1(6); 210.1(4); 195.1(5); 179(C$_{12}$H$_{19}$O,8); 152.1 (13); 151(C$_{10}$H$_{15}$O,100); 138(30); 125.1(40); 124.1(31); 123(43); 121(14); 110(24); 109(28); 107(C$_7$H$_7$O,10); 97(11); 96.1(25); 95(40); 83.1(11); 82(11); 81(20); 79(16); 69(18); 67(32); 55(38).

Analysis (%): calculated C,77.50; H,11.64; found: C,77.4;H,11.4.

Example 13

In a similar manner to Example 11, 3-(12-hydroxydodecyl)-4,4-dimethyl-2-cyclohexen-1-one was obtained.

Molecular weight: 308 ($C_{20}H_{36}O_2$)

TLC: (hexane-AcOET: 6-4) Rf=0.27

MS(EI):308(M$^+$,19);290.1(M—H$_2$O,5); 278.1(25); 263.1 (6); 252.1(6); 209.1(6); 179(C$_{12}$H$_{19}$O,8); 152.1(12); 151 (C$_{10}$H$_{15}$O,100); 138(26); 125.1(35); 124(28); 123(40); 121 (13); 110.1(18); 109(22); 96(21); 95(32); 82(10); 81(17); 79(12); 69(16); 67(25); 55(37).

Analysis (%): calculated C,77.87; H,11.76; found: C,78; H,11.7.

Example 14

In a similar manner to Example 11, 3-(13-hydroxytridecyl)-4,4-dimethyl-2-cyclohexen-1-one was obtained.

Molecular weight: 322 ($C_{21}H_{38}O_2$)

TLC: (hexane-AcOET: 6-4) Rf=0.3

GC°: Retention time: 23.4 min (purity>99%)

MS(EI):322.2(M$^+$,19);304(M—H$_2$O,6); 292.2(22); 277.1 (6); 266.1(5); 223.1(5); 179(C$_{12}$H$_{19}$O,8); 152.1(13); 151 (C$_{10}$H$_{15}$O,100); 138(25); 125.1(34); 124.1(28); 122.9(48); 121(14); 110(18); 109(23); 96.1(21); 95(33); 83.1(10); 81(18); 79(12); 69(18); 67(24); 55(40).

Analysis (%): calculated C,78.20; H,11.88; found: C,78.4; H,11.6.

Example 15

In a similar manner to Example 11, 3-(14-hydroxytetradecyl)-4,4-dimethyl-2-cyclohexen-1-one was obtained.

Molecular weight: 336 ($C_{22}H_{40}O_2$)

TLC: (hexane-AcOET: 6-4) Rf=0.3

MS(EI):336.2(M$^+$,20);318(M—H$_2$O,6); 306.2(6); 291.2 (5); 280.1(5); 237.1(5); 179.1(C$_{12}$H$_{19}$O,9); 152.1(13); 151 (C$_{10}$H$_{15}$O,100); 138(30); 125.1(33); 124(29); 122.9(56); 110(17); 109(25); 96.1(22); 95(33); 83.1(12); 81.1(19); 79(12); 69(20); 67(28); 55(40).

Analysis (%): calculated C,78.51; H,11.98; found: C,78.3; H,12.1.

Example 16

(1) Benzenesulfinic acid sodium salt (2.9 g) was added to a solution containing 1.5 g of 2-methyl-2-cyclohexen-1-one and 8 ml of water. Then 16 ml of 1N hydrochloric acid was added dropwise to the resulting mixture. The reaction mixture was stirred at room temperature for 24 hours. The crystals so precipitated were filtered and then, washed with water, isopropanol and cold ethyl ether. After recrystallization from isopropanol, 2-methyl-3-(phenylsulfonyl)-cyclohexan-1-one was obtained in the form of white crystals. Yield: 93%

2-Methyl-3-(phenylsulfonyl)-cyclohexan-1-one

Molecular weight: 252 ($C_{13}H_{16}O_3S$)

TLC: (hexane-AcOET: 6-4) Rf=0.25

$^1$H NMR (200 MHz, $CDCl_3$), major isomer(cis): δ: 1.41 (d, J=7.19 Hz,3H,H-7); 1.49–1.68 (m,1H,H-5); 1.96–2.33(m,4H,H-4,5,6e); 2.57(ddd,J=14.8 Hz,J=12.5 Hz,J=6.2 Hz,1H,H-6a); 2.85–3.01(m,1H,H-2); 3.31 (dt,$^3$J=11.2 Hz,$^3$J=4.1 Hz,1H,H-3); 7.54–7.73(m,3H,H ar.-3',4'); 7.87–7.92 (m,2H,H ar.-2').

$^{13}$C NMR (50 MHz, $CDCl_3$), two isomers are detected:

trans: δ: 14.7(C-7); 22.7(C-5);24.6(C-4); 32.6(C-6); 45(C-2); 68.2(C-3); 128.7(C ar.-2'*); 129.3(C ar.-3'*); 133.9(C ar.-4');138.2(C ar.-1'); 209.2(C-1).

cis: δ: 12.7(C-7); 20.2(C-5);23.2(C-4); 36.9(C-6); 44(C-2); 65(C-3); 128.3(C ar.-2'*); 129.3(C ar.-3'*); 133.9(C ar.-4'); 138.2(C ar.-1'); 209.2(C-1).

(2) To a solution obtained by dissolving 1.4 g of 2-methyl-3-(phenylsulfonyl)-cyclohexan-1-one in 20 ml of benzene, were added 0.41 ml of 1,2-ethanediol and 0.1 g of anhydrous paratoluenesulfonic acid. The resulting mixture was heated under reflux for 4 hours. After the reaction, a 2M aqueous sodium bicarbonate solution was added and the resulting mixture was extracted with ethyl acetate three times. The combined organic layers were washed with saturated saline and dried over magnesium sulfate. The solvent was distilled off under reduced pressure. The residue was recrystallized from ethyl ether, whereby 1,1-(ethylenedioxy)-2-methyl-3-(phenylsulfonyl)-cyclohexane was obtained in the form of white crystals. Yield: 95%

1,1-(Ethylenedioxy)-2-methyl-3-(phenylsulfonyl)-cyclohexane

Molecular weight: 296 ($C_{15}H_{20}O_4S$)

Melting point: 76 to 77° C.

TLC: (hexane-AcOET: 6-4) Rf=0.4

$^1$H NMR (200 MHz, $CDCl_3$), trans: δ: 1.24 (d, J=6.8 Hz,3H,H-7); 1.32–1.53 (m, 2H,H-5); 1.60–1.85(m,4H,H-4,6); 2.12(dqa,$^3$J=11.3 Hz,$^3$J= 6.8 Hz,1H,H-2); 3.14 (td,$^3$J=11.3 Hz,$^3$J=3.5 Hz,1H,H-3);3.83–3.99(m,4H,O—$CH_2$—$CH_2$—O); 7.49–7.68 (m,3H,H ar.-3',4'); 7.83–7.93(m,2H,H ar.-2').

cis: δ: 1.24 (d, J=7.1 Hz,3H,H-7); 1.32–1.53 (m,2H,H-5); 1.60–1.85(m,4H,H-4,6); 2.43(qad,$^3$J=7.1 Hz,$^3$J=3.6 Hz,1H,H-2); 3.34 (dt,$^3$J=12.3 Hz,$^3$J=3.6 Hz,1H,H-3); 3.83–3.99 (m,4H,O—$CH_2$—$CH_2$—O); 7.48–7.67(m, 3H,H ar.-3',4'); 7.8–7.88(m,2H,H ar.-2').

$^{13}$C NMR (50 MHz, $CDCl_3$), trans: δ: 11.7(C-7); 21.5(C-5);27.2(C-4); 34.3(C-6); 40.6 (C-2); 65.3(O—$\underline{C}H_2$—$\underline{C}H_2$—O); 67(C-3); 110(C-1); 128.5(C ar.-2'*); 129(C ar.-3'*);133.4(C ar.-4');138.7(C ar.-1').

cis: δ: 10.1(C-7); 19(C-5);21.5(C-4); 29(C-6); 36.4(C-2); 63.8(C-3); 64.3(O—$\underline{C}H_2$—$\underline{C}H_2$—O); 110.2(C-1); 128.4(C ar.-2'*); 129(C ar.-3'*); 133.4(C ar.-4'); 139(C ar.-1').

Analysis (%): calculated C,60.79; H,6.8; found: C,61; H,6.7.

(3) A solution of n-butyl lithium (1.02 ml) was added dropwise to a solution of 304 mg of 1,1-(ethylenedioxy)-2-methyl-3-(phenylsulfonyl)-cyclohexane and 4 mg of triphenylmethane in 5 ml of THF at −78° C. under an argon stream. After stirring for 10 minutes, the reaction was effected at room temperature for 1 hour. HMPA (1 ml) was added to the reaction mixture. It was then recooled to −78° C., followed by the dropwise addition of a solution of 90 mg of 10-bromo-1-decanol in 2 ml of THF. After reaction at −20° C. for 2 hours, the reaction mixture was poured into a saturated solution of ammonium chloride. The resulting mixture was extracted with ethyl ether. The organic layer was washed with water and saturated saline and dried over magnesium sulfate. The solvent was then distilled off under reduced pressure. The residue was purified by chromatography on a silica gel column while using hexane-ethyl acetate, whereby 1,2-(ethylenedioxy)-3-(10-hydroxydecyl)-2-methyl-3-(phenylsulfonyl)-cyclohexane was obtained in the form of a colorless oil. Yield: 92%

1,1-(ethylenedioxy)-3-(10-hydroxydecyl)-2-methyl-3-(phenylsulfonyl)-cyclohexane

Molecular weight: 452 ($C_{25}H_{40}O_5S$)

TLC: (hexane-AcOET: 6-4) Rf=0.2

$^1$H NMR (200 MHz, $CDCl_3$), δ: 1.14 (d,J=6.8 Hz,3H,H-17); 1.27(s large,14H,H-8 to H-14); 1.42–1.75(m,6H,H-5, 15); 1.85(qa,J=6.8 Hz,1H,H-2); 2.15–2.33(m,4H,H-4,6); 3.63(t,J=6.5 Hz,2H,H-16); 3.71–4.06(m,4H,O—$CH_2$—$CH_2$—O); 7.48–7.67(m,3H,H ar.-3',4'); 7.84–7.89(m,2H,H ar.-2').

$^{13}$C NMR (50 MHz, $CDCl_3$), δ: 7.7(C-17); 18.7(C-5); 23.7(C-14); 25(C-4); 25.6(C-7); 29.4(C-9 to C-13); 30.3(C-8); 32.6(C-15); 34.9(C-6); 43(C-2); 62.6(C-16); 64,65.5 (O—$\underline{C}H_2$—$\underline{C}H_2$—O); 72(C-3); 110.3(C-1); 128.6(C ar.-3'*); 130(C ar.-2'*); 133.3(C ar.-4'); 137.2(C ar.-1').

IR(NaCl):3515, 3063, 2926, 2853, 1585, 1286, 1140, 1098, 1083.

(4) Paratoluenesulfonic acid (20 mg) was added to a solution of 388 mg of 1,1-(ethylenedioxy)-3-(10-hydroxydecyl)-2-methyl-3-(phenylsulfonyl)-cyclohexane in 30 ml of chloroform and 6 ml of acetone. The resulting mixture was reacted at 50° C. for 24 hours. To the reaction mixture was added 10 ml of a saturated aqueous solution of sodium bicarbonate, followed by extraction with dichloromethane. The organic layer was washed with saturated saline and dried over magnesium sulfate. The solvent was distilled off under reduced pressure. The residue was purified by chromatography on a silica gel column while using hexane-ethyl acetate, whereby 3-(10-hydroxydecyl)-2-methyl-2-cyclohexen-1-one was obtained in the form of a colorless oil. Yield: 45%

3-(10-Hydroxydecyl)-2-methyl-2-cyclohexen-1-one

Molecular weight: 266 ($C_{17}H_{30}O_2$)

TLC: (hexane-AcOET: 6-4) Rf=0.2

$^1$H NMR (200 MHz, $CDCl_3$), δ: 1.27 (s large,12H,H-9 a H-14); 1.44–1.63(m,4H,H-8,15); 1.76(s,3H,H-17); 1.91 (q.J=6.3 Hz,2H,H-5); 2.18–2.41(m,6H,H-4,6,7); 3.64(t,J= 6.5 Hz,2H,H-16).

$^{13}$C NMR (50 MHz, $CDCl_3$), δ: 10.5(C-17); 22.4(C-5); 25.7(C-14); 27.3(C-4); 29.5(C-9 a C-13); 30.8(C-8); 32.7 (C-15); 35.2(C-7); 37.6(C-6); 62.8(C-16); 130.6(C-2); 159.4 (C-3); 199.6(C-1).

IR(NaCl):3455, 2926, 2853, 1665, 1620, 1450, 1120, 1055.

MS(EI): 266.2($M^+$,7); 137(51); 125(9); 124(100), 111 (15); 109(11); 96(15); 67(11); 55.1(11).

Analysis (%): calculated C,76.64; H,11.35; found: C, 76.4; H,11.7.

Example 17

In a similar manner to Example 16, 3-(11-hydroxyundecyl)-2-methyl-2-cyclohexen-1-one was obtained.

Molecular weight: 280 ($C_{18}H_{32}O_2$)

TLC: (hexane-AcOET: 6-4) Rf=0.24

MS(EI): 280.2($M^+$,6); 137(43); 125(9); 124(100), 111(14); 109(9); 96(13); 67(7); 55.1(11).

Analysis (%): calculated C,77.9; H,11.5; found: C, 76.8; H,11.3.

Example 18

In a similar manner to Example 16, 3-(12-hydroxydodecyl)-2-methyl-2-cyclohexen-1-one was obtained.

Molecular weight: 294 ($C_{19}H_{34}O_2$)

TLC: (hexane-AcOET: 6-4) Rf=0.26

MS(EI): 294.2($M^+$,6); 137(44); 125(10); 124(100), 111(14); 109(9); 96(13); 67.1(7); 55.1(11).

Analysis (%): calculated C,77.50; H,11.64; found: C, 77.6; H,11.8.

Example 19

In a similar manner to Example 16, 3-(13-hydroxytridecyl)-2-methyl-2-cyclohexen-1-one was obtained.

Molecular weight: 308 ($C_{20}H_{36}O_2$)

TLC: (hexane-AcOET: 6-4) Rf=0.28

MS(EI): 308.2($M^+$,6); 138(6); 137(40); 125(9), 124(100); 111(15); 109(8); 96(11); 55.1(10).

Analysis (%): calculated C,77.87; H,11.76; found: C, 78; H,11.5.

Example 20

In a similar manner to Example 16, 3-(14-hydroxytetradecyl)-2-methyl-2-cyclohexen-1-one was obtained.

Molecular weight: 322 ($C_{21}H_{38}O_2$)

TLC: (hexane-AcOET: 6-4) Rf=0.3

MS(EI): 322.2($M^+$,6); 137(45); 125(9); 124(100), 111(15); 109(9); 96(10); 67.1(7); 55.1(10).

Analysis (%): calculated C,78.20; H,11.88; found: C, 78.5; H,11.9.

Example 21

To a solution of 1-phenylsulfonyl-2,6,6-trimethyl-1-cyclohexene (1 g, 3.5 mmol, 2 eq.) and triphenylmethane (4 mg) in dry THF (8 ml) was added n-butyllithium (1.4 M in hexane, 4 ml, 3 eq.) at −78° C. under argon. After stirring for 10 minutes, the mixture was stirred at room temperature and HMPA (1.5 ml) was added. After 1.5 hours at this temperature, the mixture was recooled at −78° C and 11-bromo-undecanol (439 mg, 1.75 mmol, 1 eq.) was added slowly. The mixture was stirred for 3 h at −20° C. and poured into a solution of saturated $NH_4Cl$ (40 ml). The solution was extracted with ether and the organic layer was washed with brine, dried with $MgSO_4$ and concentrated in vacuo. The residue was purified by chromatography over silica gel, eluting with hexane-AcOEt (8-2 to 6-4), to give 1-(12-hydroxydodecyl-1-phenylsulfonyl)-2,6,6-trimethyl-1-cyclohexene as a white solid (622 mg, 79%).

TLC: (hexane-AcOEt: 5-5) Rf=0.43

$^1$H NMR (200 MHz, $CDCl_3$), δ: 0.87 (s 3H,H-19); 0.97(s,3H,H-20); 1.16(s, br.14H,H-10 to H-16); 1.2–1.57(m, 8H,H-4,5,9,17); 1.94(s,3H,H-21); 1.98–2.25(m,4H,H-8,3); 3.61(t,J=6.8 Hz,1H,H-18); 3.71(t,J=6.8 Hzm1HmH-7); 7.48–7.65(m,3H,H ar.-3',4'); 7.86–7.92(m,2H,H ar.-2').

$^{13}$C NMR (50 MHz), δ: 19(C-4); 23(C-21); 25.7(C-16); 28.5(C-8); 28.9(C-19,20); 29.4(C-9 to C-15); 31.2(C-17); 32.7(C-3); 35.9(C-6); 39.8(C-5); 63(C-18); 67.9(C-7); 128.4(C ar.-2'); 130.5(C-2); 133.5(C ar.-4'); 137.8(C-1); 141.8(C ar.-1').

m.p. 77–78° C.

Example 22

To a solution of 1-(12-hydroxydodecyl-1-phenylsulfonyl)-2,6,6-trimethyl-1-cyclohexene (579 mg, 1.29 mmol, 1 eq.) in dry methanol (25 ml) was added sodium phosphate dibasic $Na_2HPO_4$ (366 mg, 2 eq.) and mercury-sodium amalgam (6% Na, 4 g) at 0° C. under argon. The heterogeneous mixture was stirred at room temperature for 4 hours, then quenched with HCl 1N, extracted with ether (3 times), washed with $NaHCO_3$ saturated, dried with $MgSO_4$ and concentrated in vacuo. The residue was purified by chromatography over silica gel, eluting with hexane-AcOEt (8-2) to give 1-(12-hydroxydodecyl)-2,6,6-trimethyl-1-cyclohexene as a colorless oil (350 mg, 88%)

TLC: (hexane-AcOEt: 8-2) Rf=0.52

GC:40–280° C.(20° C./min) 10.73 min;

$^1$H NMR (200 MHz), δ: 0.96 (s,6H,H-19,20); 1.27(s,br, 16H,H-9 to H-16); 1.35–1.54(m, 8H,H-4,5,8,17); 1.57(s,3H, H-21); 1.83–2.03(m,4H,H-3,7); 3.62(t,J=6.5 Hz,2H,H-18).

$^{13}$C NMR (50 MHz), δ: 19.6(C-4); 19.8(C-21); 25.7(C-16); 28.6(C-19,20); 28.9(C-8); 29.6(C-9 to C-15); 30.5(C-17); 32.8(C-3*); 32.81(C-7*); 34.8(C-6); 39.8(C-5); 63(C-18); 126.3(C-2); 137.8(C-1).

IRv:3330(broad,O—H); 2925, 2852(w,C—H): 1466(s, C—H); 1112(s,C—O)

Example 23

To a solution of 1-(12-hydroxydodecyl)-2,6,6-trimethyl-1-cyclohexene (316 mg, 1.026 mmol) were added acetic anhydride (7 ml) and pyridine (7 ml). The mixture was stirred at room temperature for 1 hour, then quenched with HCl 5%, extracted with ether, washed with water, dried with $MgSO_4$ and concentrated in vacuo to obtain 1-(12-acetoxydodecyl)-2,6,6-trimethyl-1-cyclohexene as a colorless oil (353 mg, 98%).

TLC: (hexane-AcOEt: 5-5) Rf=0.75

GC:40–280° C.(20° C./min) 11.02;

$^1$H NMR (200 MHz), δ: 0.96 (s,6H,H-19,20); 1.27(s,br, 16H,H-9 to H-16); 1.35–1.54(m, 8H,H-4,5,8,17); 1.57(s,3H, H-21); 1.83–2.03(m,4H,H-3,7); 2.04(s,3H,$CH_3$—COO); 4.04(t,J=6.6 Hz,2H,H-18).

$^{13}$C NMR (50 MHz), δ: 19.5(C-4); 19.8(C-21); 20.9($\underline{C}H_3$—COO); 25.9(C-16); 28.6(C-19,20); 28.9(C-8); 29.6 (C-9 to C-15); 30.5(C-17); 32.7(C-7*); 32.75(C-3*); 34.8 (C-6); 39.9(C-5); 64.6(C-18); 126.3(C-2); 137.8(C-1); 171.2 ($CH_3$—$\underline{C}$OO).

IR v: 2925, 2852(w,C—H): 1744(w,C=O); 1466(s,C—H); 1238(w,C—O)

Example 24

To a solution of 1-(12-acetoxydodecyl)-2,6,6-trimethyl-1-cyclohexene (321 mg, 0.92 mmol, 1 eq.) in cyclohexane (6 ml) was added water (0.8 ml), ruthenium trichloride hydrate (0.7% mol, 1.3 mg) and 70% t-BuOOH (1.26 ml, 10 eq.). The solution was stirred at room temperature for 6 hours, filtered through a pad of celite and poured into a solution of 10% $Na_2SO_3$. The solution was extracted with ether, washed with brine, dried with $MgSO_4$ and concentrated in vacuo. The residue was purified by chromatography over silica gel, eluting with hexane-AcOEt (95-15 to 90-10) to give 3-(12- acetoxydodecyl)-2,4,4-trimethyl-2-cyclohexen-1-one as a colorless oil (227 mg, 53%).

TLC: (hexane-AcOEt: 3-7) Rf=0.68

GC:40–280° C.(20° C./min) 12.2 min, 99%;

$^1$H NMR (200 MHz), 67 :1.13 (s,6H,H-19,20); 1.26(s,br, 16H,H-9 to H-16); 1.35–1.69(m, 4H,H-8,17); 1.73(s,3H,H-21); 1.78(t,J=7.5 Hz,2H,H-5); 2.02(s,3H,$CH_3$—COO); 2.11–2.19(m,2H,H-7); 2.43(t,J=6.8 Hz,2H,H-6); 4.03(t,J= 6.8 Hz,2H,H-18).

$^{13}$C NMR (50 MHZ), δ: 11.5(C-21); 20.9($\underline{C}H_3$—COO); 25.8(C-16); 26.8(C-19,20); 28.8(C-8); 29.1(C-17); 29.5(C-9 to C-15); 30.45(C-7); 34.2(C-5); 36.2(C-4); 37.3(C-6); 64.5 (C-18); 130.5(C-2); 165(C-3); 171($CH_3$—$\underline{C}$OO); 199(C-1).

IR v: 2925, 2852(w,C—H): 1741(w,C=O); 1667(w,C—O); 1607(s,C—C); 1468(s,C—H); 1239(w,C—O).

Example 25

To a solution of 3-(12-acetoxydodecyl)-2,4,4-trimethyl-2-cyclohexene-1-one (132 mg, 0.36 mmol, 1 eq.) in dry methanol (8 ml) was added water (3 drops) and $K_2CO_3$ (74 mg, 0.54 mmol, 1.5 eq.). After stirring at room temperature for 2.5 hours the solution was neutralized at pH 7 with HCl 5%, extracted with ether, dried with $MgSO_4$ and concentrated in vacuo. The residue was purified by chromatography over silica gel, eluting with hexane-AcOEt (8-2 to 7-3) to give 3-(12-hydroxydodecy)-2,4,4-trimethyl-2-cyclohexen-1-one as a colorless oil (94 mg, 81%).

TLC: (hexane-AcOEt: 7-3) Rf=0.2

GC:40–280° C.(20° C./min) 12 min, 99%;

$^1$H NMR (200 MHz), δ: 1.13 (s,6H,H-19,20); 1.26(s,br, 16H,H-9 to H-16); 1.35–1.69(m, 4H,H-8,17); 1.73(s,3H,H-21); 1.77(t,J=7.5 Hz,2H,H-5); 2.11–2.19(m,2H,H-7); 2.43(t, J=6.8 Hz,2H,H-6); 3.61(t,J=6.8 Hz,2H,H-18).

$^{13}$C NMR (50 Mhz), δ: 11.4(C-21); 25.7(C-16); 26.8(C-19,20); 28.8(C-8); 29.5(C-9 to C-15); 30.45(C-7); 32.7(C-17); 34.2(C-5); 36.2(C-4); 37.3(C-6); 62.9(C-18); 130.4(C-2); 165.4(C-3); 199(C-1).

IR v: 3440 (broad OH); 2925, 2852(w,C—H) : 1666(w, C=O); 1605(s,C=C); 1467(s,C—H).

Examples 26–29

In a manner similar to each of Examples 21–25, the following compounds are obtained. The parenthetical values indicate Rf values of TLC at hexane: ethylacetate=7.3.

Example 26

3-(13-hydroxytridecyl)-2,4,4-trimethyl-2-cyclohexen-1-one (Rf=0.2)

Example 27

3-(14-hydroxytetradecyl)-2,4,4-trimethyl-2-cyclohexen-1-one (Rf=0.25)

Example 28

3-(15-hydroxypentadecyl)-2,4,4-trimethyl-2-cyclohexen-1-one (Rf=0.29)

Example 29

3-(16-hydroxyhexadecyl)-2,4,4-trimethyl-2-cyclohexen-1-one (Rf=0.26)

Test: Neurite Growth Stimulating Effects

Cultures were performed in accordance with the method as announced by the present inventors [Borg J., et al. Dev. Brain Res. 18, 37(1985)] by using neurons derived from fetal rat cerebral hemisphere. The dissociated cells were seeded at a density of $1.5 \times 10^5$ cells per dish coated with 35-mm polylysine. To the dish, a DMEM culture medium supplemented with insulin, transferrin, progesterone, sodium selenite and putescine was added. Each compound was dissolved in ethanol to $5 \times 10^{-8}$ M and cells were cultured without medium change for 3 days. Cultures were then fixed with 2% glutaraldehyde in PBS and neurons were observed and photographed under a phase-contrast microscope. The results are shown in Table 1.

TABLE 1

| Compound | Influence on neurite growth |
|---|---|
| Negative control | 0 |
| Example 8 | +++ |
| Example 9 | ++++ |
| Example 10 | ++++ |
| Example 12 | ++ |
| Example 13 | +++ |
| Example 14 | +++ |
| Example 15 | +++ |
| Example 18 | ++ |
| Example 19 | +++ |
| Example 20 | ++++ |
| Example 27 | ++++ |
| Example 28 | ++++ |
| Fibroblast growth factor | ++ |

0: no effect, +: slight effect, ++: moderate effect, +++: strong effect >160%, ++++: very stron effect >200%, –: toxic, ––: very toxic As apparent from Table 1, it has been found that the invention compound (1) has excellent neurite growth stimulating effects even in a markedly low dose.

Industrial Applicability

The invention compound (1) exhibits strong neurite growth stimulating effects so that it is useful as a preventive and/or therapeutic for Alzheimer's disease and the like diseases.

What is claimed is:

1. A method of treating dementia in a patient comprising administering an effective amount of a cyclohexenone long-chain alcohol represented by the formula (1):

(1)

wherein $R^1$, $R^2$, and $R^3$ each independently represents a hydrogen atom or a methyl group
and X represents a $C_{10-18}$ alkylene to a patient in need thereof.

2. The method of claim 1, wherein said administering is through an oral route.

3. The method of claim 1, wherein said administering is through an parenteral route.

4. The method of claim 1, wherein said dementia is Alzheimer's disease.

5. The method of claim 1, wherein said patient is a human patient.

6. The method of claim 1, wherein said effective amount is from 0.01 to 100 mg/day.

7. A method of stimulating neurite outgrowth in patient comprising administering an effective amount of a cyclohexenone long-chain alcohol represented by the formula (1):

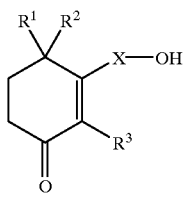

(1)

wherein $R^1$, $R^2$, and $R^3$ each independently represents a hydrogen atom or a methyl group
and X represents a $C_{10-18}$ alkylene group.

8. The method of claim 7, wherein said administering is through an oral route.

9. The method of claim 7, wherein said administering is through an parenteral route.

10. The method of claim 7, wherein said dementia is Alzheimer's disease.

11. The method of claim 7, wherein said patient is a human patient.

12. The method of claim 7, wherein said effective amount is from 0.01 to 100 mg/day.

13. The method of claim 1, wherein said cyclohexenone long-chain alcohol is selected from the group consisting of 3-(10-hydroxydecyl)-2-cyclohexen-1-one;

3-(11-hydroxy-undecyl)-2-cyclohexen-1-one;
3-(12-hydroxy-dodecyl)-2-cyclohexen-1-one;
3-(13-hydroxy-tridecyl)-2-cyclohexen-1-one;
3-(14-hydroxy-tetradecyl)-2-cylcohexen-1-one;
3-(10-hydroxydecyl)-4-methyl-2-cyclohexen-1-one;
3-(11-hydroxy-undecyl)-4-methyl-2-cyclohexen-1-one;
3-(12-hydroxy-dodecyl)-4-methyl-2-cyclohexen-1-one;
3-(13-hydroxy-tridecyl)-4-methyl-2-cyclohexen-1-one;
3-(14-hydroxy-tretradecyl)-4-methyl-2-cyclohexen-1-one;
4,4-dimethyl-3-(10-hydroxydecyl)-2-cyclohexen-1-one;
3-(11-hydroxy-undecyl)-4,4-dimethyl-2-cyclohexen-1-one;
3-(12-hydroxy-dodecyl)-4,4-dimethyl-2-cyclohexen-1-one;
3-(13-hydroxy-tridecyl)-4,4-dimethyl-2-cyclohexen-1-one;
3-(14-hydroxy-tetradecyl)-4,4-dimethyl-2-cyclohexen-1-one;
3-(10-hydroxydecyl)-2-methyl-2-cyclohexen-1-one;
3-(10-hydroxylundecyl)-2-methyl-2-cyclohexen-1-one;
3-(12-hydroxy-dodecyl)-2-methyl-2-cyclohexen-1-one;
3-(13-hydroxy-tridecyl)-2-methyl-2-cyclohexen-1-one;
3-(14-hydroxy-tetradecyl)-2-methyl-2-cyclohexen-1-one;
3-(12-hydroxydodecyl)-2,4,4-trimethyl-2-cyclohexen-1-one;
3-(13-hydroxytridecyl)-2,4,4-trimethyl-2-cyclohexen-1-one;
3-(14-hydroxytetradecyl)2,4,4-trimethyl-2-cyclohexen-1-one;
3-(15-hydroxypentadecyl)-2,4,4-trimethyl-2-cyclohexen-1-one; and
3-(16-hydroxyhexadecyl)-2,4,4-trimethyl-2-cyclohexen-1-one.

14. The method of claim 13, wherein said cyclohexenone long-chain alcohol is selected from the group consisting of:

3-(12-hydroxy-dodecyl)-4-methyl-2-cyclohexen-1-one;
3-(12-hydroxy-tridecyl)-4-methyl-2-cyclohexen-1-one;
3-(14-hydroxy-tetradecyl)-4-methyl-2-cyclohexen-1-one;
3-(11-hydroxy-undecyl)-4,4-dimethyl-2-cyclohexene-1-one;
3-(12-hydroxy-dodecyl)-4,4-dimethyl-2-cyclohexen-1-one;
3-(13-hydroxy-tridecyl)-4,4-dimethyl-2-cyclohexen-1-one;
3-(14-hydroxy-tetradecyl)-4,4-dimethyl-2-cyclohexen-1-one;
3-(12-hydroxy-dodecyl)-2-methyl-2-cyclohexen-1-one;
3-(13-hydroxy-tridecyl)-2-methyl-2-cyclohexen-1-one;
3-(14-hydroxy-tetradecyl)-2-methyl-2-cyclohexen-1-one;
3-(14-hydoxytetradecyl)-2,4,4-trimethyl-2-cyclohexen-1-one; and
3-(15-hydroxypentadecyl)-2,4,4-trimethyl-2-cyclohexen-1-one.

15. The method of claim 7, wherein said cyclohexenone long-chain alcohol is selected from the group consisting of 3-(10-hydroxydecyl)-2-cyclohexan-1-one;

3-(11-hydroxy-undecyl)-2-cyclohexen-1-one;
3-(12-hydroxy-dodecyl)-2-cyclohexen-1-one;
3-(13-hydroxy-tridecyl)-2-cyclohexen-1-one;
3-(14-hydroxy-tetradecyl)-2-cylcohexen-1-one;
3-(10-hydroxydecyl)-4-methyl-2-cyclohexen-1-one;
3-(11-hydroxy-undecyl)-4-methyl-2-cyclohexen-1-one;
3-(12-hydroxy-dodecyl)-4-methyl-2-cyclohexen-1-one;
3-(13-hydroxy-tridecyl)-4-methyl-2-cyclohexen-1-one;
3-(14-hydroxy-tetradecyl)-4,4-methyl-2-cyclohexen-1-one;
4,4-dimethyl-3-(10-hydroxydecyl)-2-cyclohexen-1-one;
3-(11-hydroxy-undecyl)-4,4-dimethyl-2-cyclohexen-1-one;
3-(12-hydroxy-dodecyl)-4,4-dimethyl-2-cyclohexen-1-one;
3-(13-hydroxy-tridecyl)-4,4-dimethyl-2-cyclohexen-1-one;
3-(14-hydroxy-tetradecyl)-4,4-dimethyl-2-cyclohexen-1-one;
3-(10-hydroxydecyl)-2-methyl-2-cyclohexen-1-one;
3-(11-hydroxylundecyl)-2-methyl-2-cyclohexen-1-one;
3-(12-hydroxy-dodecyl)-2-methyl-2-cyclohexen-1-one;
3-(13-hydroxy-tridecyl)-2-methyl-2-cyclohexen-1-one;
3-(14-hydroxy-tetradecyl)-2-methyl-2-cyclohexen-1-one;
3-(12-hydroxydodecyl)-2,4,4-trimethyl-2-cyclohexen-1-one;
3-(13-hydroxytridecyl)-2,4,4-trimethyl-2-cyclohexen-1-one;
3-(14-hydroxytetradecyl)2,4,4-trimethyl-2-cyclohexen-1-one;
3-(15-hydroxypentadecyl)-2,4,4-trimethyl-2-cyclohexen-1-one; and
3-(16-hydroxyhexadecyl)-2,4,4-trimethyl-2-cyclohexen-1-one.

16. A cyclohexenone long-chain alcohol selected from the group consisting of 3-(10--hydroxydecyl)-2-cyclohexen-1-one;
3-(11-hydroxy-undecyl)-2-cyclohexen-1-one;
3-(12-hydroxy-dodecyl)-2-cyclohexen-1-one;
3-(13-hydroxy-tridecyl)-2-cyclohexen-1-one;
3-(14-hydroxy-tetradecyl)-2-cylcohexen-1-one;
3-(10-hydroxydecyl)-4-methyl-2-cyclohexen-1-one;
3-(11-hydroxy-undecyl)-4-methyl-2-cyclohexen-1-one;
3-(12-hydroxy-dodecyl)-4-methyl-2-cyclohexen-1-one;
3-(13-hydroxy-tridecyl)-4-methyl-2-cyclohexen-1-one;

3-(14-hydroxy-tretradecyl)-4-methyl-2-cyclohexen-1-one;
4,4-dimethyl-3-(10-hydroxydecyl)-2-cyclohexen-1-one;
3-(11-hydroxy-undecyl)-4,4-dimethyl-2-cyclohexen-1-one;
3-(12-hydroxy-dodecyl)-4,4-dimethyl-2-cyclohexen-1-one;
3-(13-hydroxy-tridecyl)-4,4-dimethyl-2-cyclohexen-1-one;
3-(14-hydroxy-tetradecyl)-4,4-dimethyl-2-cyclohexen-1-one;
3-(10-hydroxydecyl)-2-methyl-2-cyclohexen-1-one;
3-(11-hydroxylundecyl)-2-methyl-2-cyclohexen-1-one;
3-(12-hydroxy-dodecyl)-2-methyl-2-cyclohexen-1-one;
3-(13-hydroxy-tridecyl)-2-methyl-2-cyclohexen-1-one;
3-(14-hydroxy-tetradecyl)-2-methyl-2-cyclohexen-1-one;
3-(12-hydroxydodecyl)-2,4,4-trimethyl-2-cyclohexen-1-one;
3-(13-hydroxytridecyl)-2,4,4-trimethyl-2-cyclohexen-1-one;
3-(14-hydroxytetradecyl)2,4,4-trimethyl-2-cyclohexen-1-one;
3-(15-hydroxypentadecyl)-2,4,4-trimethyl-2-cyclohexen-1-one; and
3-(16-hydroxyhexadecyl)-2,4,4-trimethyl-2-cyclohexen-1-one.

17. A pharmaceutical composition comprising at least one cyclohexenone long-chain alcohol of claim 16 and a pharmaceutically acceptable carrier.

* * * * *

UNITED STATES PATENT AND TRADEMARK OFFICE
CERTIFICATE OF CORRECTION

PATENT NO.   : 6,228,893 B1
DATED        : May 8, 2001
INVENTOR(S)  : Bang Luu et al.

It is certified that error appears in the above-identified patent and that said Letters Patent is hereby corrected as shown below:

Column 23,
Line 48, "tretradecyl" should read -- tetradecyl --;
Line 58, "10" should read -- 11 --.

Column 24,
Line 24, "cyclohexan" should read -- cyclohexen --;
Line 33, "methyl" should read -- dimethyl --;
Line 36, "-4-" should read -- 4,4 --.

Column 25,
Line 1, "tretradecyl" should read -- tetradecyl --.

Signed and Sealed this

Fourteenth Day of May, 2002

Attest:

JAMES E. ROGAN
Attesting Officer   Director of the United States Patent and Trademark Office